United States Patent [19]
Bissett et al.

[11] Patent Number: 5,821,237
[45] Date of Patent: *Oct. 13, 1998

[54] COMPOSITIONS FOR VISUALLY IMPROVING SKIN

[75] Inventors: Donald Lynn Bissett, Hamilton; Gerald Bruce Kasting, Wyoming, both of Ohio; Kay Lesley Powers, Lawrenceburg, Ind.

[73] Assignee: The Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 552,140

[22] Filed: Dec. 11, 1995

Related U.S. Application Data

[63] Continuation-in-part of Ser. No. 480,632, Jun. 7, 1995, Pat. No. 5,681,852.

[51] Int. Cl.$^6$ .......................... A61K 31/095; A61K 31/19; A61K 31/66; A61K 31/685
[52] U.S. Cl. .............................. 514/75; 514/77; 514/102; 514/440; 514/550; 514/562; 514/572; 514/709; 514/706; 514/729
[58] Field of Search ................................ 514/75, 77, 102, 514/440, 550, 562, 572, 706, 709, 729

[56] References Cited

U.S. PATENT DOCUMENTS

| | | | |
|---|---|---|---|
| 3,647,834 | 3/1972 | Martin et al. | 514/859 |
| 4,411,886 | 10/1983 | Hostettler | 424/70 |
| 4,732,892 | 3/1988 | Sarpotdar et al. | 514/178 |
| 4,847,071 | 7/1989 | Bissett et al. | 424/59 |
| 4,847,072 | 7/1989 | Bissett et al. | 424/59 |
| 4,945,094 | 7/1990 | Salim | 514/264 |
| 5,100,908 | 3/1992 | Murata et al. | 514/396 |
| 5,296,500 | 3/1994 | Hildebrand | 514/562 |
| 5,434,144 | 7/1995 | Kasting et al. | 514/76 |

FOREIGN PATENT DOCUMENTS

| | | |
|---|---|---|
| 259249 | 3/1988 | European Pat. Off. . |
| 0288112 | 9/1988 | European Pat. Off. . |
| 0299756A2 | 1/1989 | European Pat. Off. . |
| 380410 | 8/1990 | European Pat. Off. . |
| 0440298 | 8/1991 | European Pat. Off. . |
| 0633308A1 | 1/1995 | European Pat. Off. . |
| 2154504 | 5/1973 | France . |
| 3610394 | 10/1987 | Germany . |
| 56-147708 | 11/1981 | Japan . |
| 59-5107 | 1/1984 | Japan . |
| 06092833 | 4/1994 | Japan . |
| 06135825 | 5/1994 | Japan . |
| 6157257 | 6/1994 | Japan . |
| 1283892 | 3/1975 | United Kingdom . |
| 1488448 | 10/1977 | United Kingdom . |
| 1518683 | 7/1978 | United Kingdom . |
| 2177917 | 2/1987 | United Kingdom . |
| WO 91/17237 | 11/1991 | WIPO . |
| WO 93/03697 | 3/1993 | WIPO . |
| WO 93/10755 | 6/1993 | WIPO . |
| WO 94/04129 | 3/1994 | WIPO . |
| WO 94/05255 | 3/1994 | WIPO . |
| WO 94/05279 | 3/1994 | WIPO . |
| WO 94/05302 | 3/1994 | WIPO . |
| WO 94/09755 | 5/1994 | WIPO . |
| WO 94/14421 | 7/1994 | WIPO . |
| WO 95/00136 | 1/1995 | WIPO . |
| WO 95/13048 | 5/1995 | WIPO . |

OTHER PUBLICATIONS

Merck Index, 11th Ed., p. 79 (Merck) 1993.

Ohshima et al., "Enhancing Effect of Absorption Promoters on Percutaneous Absorption of a Model Dye (6–Carboxyflulorescein) as Poorly Absorbable Drugs. I. Comparison of Plasma Levels After Addition of Various Absorption Promoters in Rat", *J Pharm. Dyn.*, vol.7, pp. 648–655, 1984.

Kushida et al., "Application of Calcium Thioglycolate to Improve Transdermal Delivery of Theophylline in Rats", *Chem. Pharm. Bull.*, vol. 32, pp. 268–274, 1984.

Ohshima et al., "Enhancing Effect of Absorption Promoters on Percutaneous Absorption of a Model Dye (6–Carboxyfluorescein) as a Poorly Absorbable Drug. III. Histological Study After Addition of Various Absorption Promoters in Rats", *J. Pharmacobio–Dyn.*, vol. 9, pp. 223–228, 1986.

Nishihata et al., "Effects of Dithiothreitol and Ascorbate on the Penetration of Diclofenac Across Excised Rat Dorsal Skin", *Pharmaceutical Research*, vol. 5, No. 11, pp. 738–740, 1988.

Goates et al., "Enhanced Permeation and Stratum Corneum Structural Alterations in the Presence of Dithiothreitol", *Biochimica et Biophysica Acta*, vol. 1153, pp. 289–298, 1993.

Bennett, "Transdermal Drug Permeation Enhancement Using Low Molecular Weight Primary Aliphatic Thiols", Medical U. of S. Carolina, Dissertation, 1991.

Lei, "Extraction of Phytic Acid and its Application to Ordinary Chemical Engineering", *Riyong Huaxue Gongye*, vol. 5, pp. 223–224, 1989.

*J. of the American College of Toxicology*, vol. 10, No. 1, pp. 33–52, 1991.

*Primary Examiner*—Phyllis G. Spivack
*Attorney, Agent, or Firm*—Loretta J. Henderson; George W. Allen; David L. Suter

[57] ABSTRACT

The subject invention relates to compositions which are useful for improving the visual appearance of skin, especially facial skin. The composition contains certain primary actives including at least one cyclic polyanionic polyols at least one sulfhydryl compound and at least one zwitterionic surfactant. The subject invention further relates to methods of improving the visual appearance of skin.

24 Claims, No Drawings

COMPOSITIONS FOR VISUALLY IMPROVING SKIN

This is a continuation-in-part of application Ser. No. 08/480,632, filed on Jun. 7, 1995 now U.S. Pat. No. 5,681,852.

TECHNICAL FIELD

The subject invention relates to the field of skin compositions for improving the appearance of skin. More specifically, the present invention relates to compositions and methods for improving the appearance of skin, particularly facial skin, e.g., providing a more uniform and desirable visual perception of the skin.

BACKGROUND OF THE INVENTION

More and more commonly, the population is concerned with the improvement of the condition of skin and particularly the appearance of skin, more particularly facial skin. Thus, there is high interest in decreasing the visual appearance of skin flaws and in increasing the evenness of skin. More particularly, there is an increasing and high interest in the slowing and/or alleviation of the visual evidence of aging skin. For example, aging skin is typically characterized by one or more of fine lines, wrinkles, age spots, dryness, scaling, loss of skin tone, sagging, enlarged pores, sallowness and the like. Slowing the visual appearance of a condition involves a decrease in the rate of appearance of such condition and is generally preventative, alleviation of the visual appearance of a condition involves treatment of an existing condition so as to result in a decreased visual appearance of such condition.

Several approaches to improve skin condition have been taken over the years. Recently, compositions have been described as being useful for regulating skin wrinkles or repairing skin. For example, see U.S. Pat. No. 5,296,500, issued to Greg G. Hillebrand on Mar. 22, 1994, and U.S. Pat. No. 5,434,144, issued to Gerald B Kasting and John M. Gardlik on Jul. 18, 1995.

While many of the compositions known in the art have provided some benefit with regard to skin appearance, there is an ongoing need to provide improved compositions for the improvement of skin appearance, more particularly decreasing the appearance of skin flaws and increasing the evenness of skin. Even more particularly, there is an increasing and high interest in the slowing and/or alleviation of the visual evidence of aging skin. There is a particular need to provide such improved compositions which are also mild to the skin.

It is therefore an object of the subject invention to provide topical compositions for improving the visual appearance of mammalian skin.

It is further object of the subject invention to provide such compositions which slow the onset of and/or alleviate the visual appearance of one or more skin conditions accompanying aging skin, including those conditions described above.

It is yet another object to provide compositions for regulating skin wrinkles, e.g., which slow the onset of an/or alleviate the visual appearance of fine lines and/or wrinkles in mammalian skin.

It is also an object of the subject invention to provide methods for improving the visual appearance of mammalian skin, for regulating wrinkles in mammalian skin, and for regulating atrophy of mammalian skin.

It is yet another object to provide such compositions which are also mild to the skin.

Other objects of the subject invention will be apparent from the disclosure which follows.

SUMMARY OF THE INVENTION

The subject invention involves compositions which are useful for improving the appearance of skin. The compositions contain a polar skin repair active, a sulfhydryl compound, and a zwitterionic surfactant. Preferred compositions contain as primary actives:

(a) one or more polar skin repair actives selected from the group consisting of cyclic polyanionic polyols or a derivative thereof, sulfated saccharides, sulfated glycosaminoglycans, sulfonated saccharides, sulfated cyclodextrins, sulfonated cyclodextrins, peptides selected from the group consisting of tribasic tripeptides, tribasic tetrapeptides, His-Gly-Gly, Iamin, phosphorylated saccharides, phosphorylated cyclodextrins, phosphonated saccharides, phosphonated cyclodextrins, polycarboxylate saccharides, polycarboxylate cyclodextrins, and charged phospholipids;

(b) one or more sulfhydryl compound(s) selected from the group consisting of N-acetylcysteine, cysteine, glutathione, thioglycolic acid, thioglycolic acid ethyl ester, thiosalicyclic acid, cysteamine, dithiothreitol, lipoic acid, dithioerythritol, thioacetic acid, thiolactic acid, mercaptoethanol, dimercaptol, monothioglycerol, N-(2-mercaptoproprionyl)glycine, bucillamine, mercaptomenthone, and cosmetically acceptable derivatives thereof; and (c) one or more zwitterionic surfactant(s) having the structure:

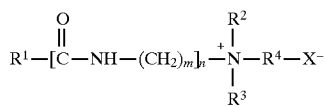

wherein
(1) $R^1$ is unsubstituted, saturated or unsaturated, straight or branched chain alkyl having from about 9 to about 22 carton atoms;
(2) m is an integer from 1 to 3;
(3) n is 0 or 1;
(4) $R^2$ and $R^3$ are, independently, alkyl having from 1 to about 3 carbon atoms, unsubstituted or mono-substituted with hydroxy;
(5) $R^4$ is saturated or unsaturated, straight or branched chain alkyl, which is unsubstituted or mono-substituted with hydroxy, having from 1 to about 5 carbon atoms; and
(6) X is $CO_2$, $SO_3$ or $SO_4$;
and cosmetically acceptable salts thereof.

It has surprisingly been found that the compositions of the present invention tend to exhibit benefits in the visual improvement of skin which are synergistic relative to comparable compositions containing only one or two of the specified groups of primary actives (namely compositions that do not include the polar skin repair active, the sulfhydryl compound, or the zwitterionic surfactant). In addition to having synergistic efficacy, the compositions are mild to the skin.

The subject invention is also directed to a method of improving the visual appearance of skin, especially a method of regulating wrinkles in mammalian skin.

These and other features, aspects and advantages of the subject invention will become better understood with reference to the following description and appended claims.

DETAILED DESCRIPTION OF THE INVENTION

The compositions of the present invention are useful as topical compositions, i.e., they are suitable for topical administration to a biological subject such as a mammal. The compositions of the subject invention are administered topically to a biological subject, i.e., by depositing the composition on the skin of the subject (e.g., by the direct laying on, spraying on or spreading of the composition on the skin). Topical application involves the deposition of a safe and effective amount of the primary actives on the skin (safe and effective amounts of the primary actives are left in contact with the skin).

The topical compositions comprise a safe and effective amount of the primary active agents and a cosmetically acceptable topical carrier for the actives.

As used herein "comprising" means that other steps and ingredients which do not affect the end result can be added. This term encompasses the terms "consisting of" and "consisting essentially of".

As used herein, "safe and effective amount" means a sufficient amount of a compound, composition or other material described by this phrase to significantly induce a positive modification in the skin condition being treated, but low enough to avoid serious side effects (at a reasonable benefit/risk ratio), within the scope of sound judgment of the skilled artisan. The safe and effective amount of the compound, composition or other material may vary with the particular skin condition being treated, the age of the biological subject being treated, the severity of the condition, the duration of the treatment, the nature of concurrent therapy, the specific compound, composition or other material employed, the particular cosmetically acceptable carrier utilized, and like factors within the knowledge and expertise of the skilled artisan.

As used herein, "primary actives," and "primary active agents" means a combination of at least one of the polar skin repair actives, sulfhydryl compounds, and zwitterionic surfactants having structure (I) described herein. As used herein, "polar skin repair active" means an active which improves the visual appearance of skin and which has a full or multiple ionic charge.

As used herein, "cosmetically acceptable" means that a material (e.g., compound or composition) which the phrase describes is suitable for use in contact with the tissues of humans and lower animals without undue toxicity, incompatibility, instability, irritation, allergic response and the like, commensurate with a reasonable benefit/risk ratio.

By "improving the visual appearance of skin", it is meant that one or more of the following benefits are achieved: reducing the visual appearance of pores (e.g., by reducing the size of pores), reducing imperfections and/or blemishes in skin color, including lightening hyperpigmented regions of skin or evening pigmentation, relieving dryness, eliminating dry rough spots, improving the skin's ability to retain moisture and/or protect itself from environmental stresses, reducing the appearance of fine lines and wrinkles, improving appearance and skin tone, increasing skin firmness and/or suppleness, decreasing skin sagging, increasing skin glow and clarity, increasing the skin renewal process, and/or removing vellus hair. Improving the visual appearance of skin may involve, for example, regulating wrinkles, regulating atrophy, skin lightening, regulating skin smoothness, and/or reducing the visual appearance of pores.

As used herein, "regulating wrinkles" means preventing, retarding, arresting, or reversing the process of wrinkle or fine line formation or diminishing the visual appearance and/or size of wrinkles or fine lines tin mammalian skin. Preferred regulation of wrinkles involves diminishing the size of existing wrinkles and/or fine lines, i.e., reducing at least one dimension of wrinkles and/or fine lines, e.g., reducing the depth, length and/or width of existing wrinkles and/or fine lines. Regulating wrinkles may involve minimizing, alleviating, or slowing the onset of fine lines and/or wrinkles which are capable of being perceived with or without magnification. Other manifestations often associated with regulating wrinkles are a smoother feel and/or improved texture to the skin.

As used herein "regulating atrophy" means preventing, retarding, arresting or reversing the process of atrophy in mammalian skin.

As used here, "skin lightening" and "lightening the skin" means decreasing melanin in skin, including one or more of lightening of hyperpigmented skin regions including age spots, melasma, chloasma, freckles, post inflammatory hyperpigmentation or sun-induced pigmented blemishes. As used herein, "hyperpigmented region" means a localized region of darker skin, relative to basal skin tone. For example, the hyperpigmented region may be a localized region of high melanin content.

As used herein, "regulating skin smoothness" means decreasing tactile and/or visual roughness and increasing tactile and/or visual smoothness of skin. Regulating skin smoothness may decrease the dry appearance of skin. The decrease in roughness and increase in smoothness may result in a more uniform gliding of the fingers over the skin.

As used herein, "vellus hair" means a fine, short hair of less than 1 cm in length, containing little or no pigmentation. In comparison, "terminal hair" means coarse, pigmented, medullated hair which in its natural state is generally longer than a vellus hair (e.g., as seen on the scalp, eyebrows, eyelashes and secondary sexual hair).

As used herein, "leave-on" means a composition that is topically applied without washing off for a period of typically at least several hours, e.g., 4–12 hours, before the skin might be washed. In contrast a "rinse-off" composition is intended to be rinsed from the skin soon after application of the composition, generally within about 30 minutes after application of the composition (e.g., a facial cleanser or a shower gel). Such rinse-off compositions are formulated so as to deposit an effective amount of primary actives on the skin.

Primary Actives

Polar Skin Repair Active

Polar skin repair actives that are suitable for use herein are selected from the group consisting of cyclic polyanionic polyols, sulfated saccharides, sulfonated saccharides, sulfated glycosaminoglylcans, sulfated cyclodextrins, sulfonated cyclodextrins, peptides selected from tribasic tripeptides, tribasic tetrapeptides, His-Gly-Gly, and Iamin, phosphorylated saccharides, phosphorylated cyclodextrins, phosphonated saccharides, phosphonated cyclodextrins polycarboxylate saccharides, polycarboxylate cyclodextrins, charged phospholipids, and combinations thereof. Such actives, when used alone, are generally poorly delivered to the skin. Delivery of such actives to the skin tends to be enhanced by the present compositions. Preferred polar skin repair actives include the cyclic polyanionic polyols or derivatives described herein, sulfated saccharides, sulfated cyclodextrins, sulfonated cyclodextrins, and the peptides.

The cyclic polyanionic polyols, sulfated saccharides, sulfated glycosaminoglycans, sulfonated saccharides, sulfated cyclodextrins, sulfonated cyclodextrins, peptides, phosphorylated saccharides, phosphorylated cyclodextrins, phosphonated saccharides, phosphonated cyclodextris, polycarboxylate saccharides, polycarboxylate cyclodextrins and charged phospholipids are particularly effective for regulating skin wrinkles, especially effacing existing wrinkles or fine lines, regulating atrophy, and/or for reducing the sallow appearance of skin. The cyclic polyanionic polyols are also effective in evening skin tone, particularly in reducing under-eye circles.

Cyclic polyanionic polyols or derivatives thereof which are suitable for use herein are those having the structure:

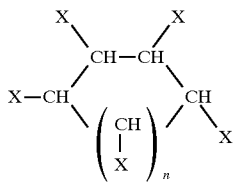

wherein n is 1, 2 or 3 and each X is, independently, selected from the group consisting of $OSO_3^-$, $OPO_3^{2-}$, $SO_3^-$, $PO_3^{2-}$, $CO_2^-$, and OH. At least three X are other than OH, ore preferably at least four X, more preferably still at least five X, most preferably six X. When n is 1 or 2, all X are, preferably other than OH. All X which are other than OH are preferably the same. Cyclic polyanionic polyols and derivatives of this type which are suitable for use herein are described in U.S. Pat. No. 5,434,144, issued to Kasting and Gardlik on Jul. 18, 1995, incorporated herein by reference.

The cyclic polyanionic polyol or derivative is neutralized by an appropriate amount of a pharmaceutically-acceptable cation so as to balance the charge. The cation is selected from a group including (but are not limited to) $H^+$, $Na^+$, $K^+$, $Ca^{++}$, $Mg^{++}$, $Al_2(OH)_5^+$, $NH_4^+$, $(HOCH_2CH_2)_3NH^+$, $(CH_3CH_2)NH^+$, $HOCH_2(CH_3)_2CNH_3^+$, $(HOCH_2)_3CNH_3^+$, $CH_3(HOCH_2)_2CNH_3^+$, $CH_3CH_2(HOCH_2)_2CNH_3^+$, $(CH_3CH_2)_4N^+$, $C_{16}H_{33}(CH_3)_3N^+$ and $(N-C_{16}H_{33})C_5H_4N^+$, and mixtures thereof.

Sulfated saccharides that are suitable for use herein include sucrose ostasulfate, sorbitol hexasulfate, trehalose sulfate, inositol hexasulfate, dulcitol hexasulfate, mannitol hexasulfate, ribitol pentasulfate, xylitol pentasulfate, D-threitol tetrasulfate, pentaerythritol tetrasulfate, meso-erythritol tetrasulfate, glycerol trisulfate, dextran sulfate, and combinations thereof. In general, the more sulfation the greater the improvement in skin appearance. Preferred sulfated saccharides contain at least five sulfate groups. Sucrose octasulfate is preferred.

Sulfated glycosaminoglycans that are suitable for use herein include heparin, heparan sulfate, dermatan sulfate, sulodexide, mesoglycan, and combinations thereof.

Sulfated or sulfonated cyclodextrins that are suitable for use herein include alpha, beta, and gamma cyclodextrins with an average degree of substitution of from about 4 to about 12, 14 or 16, respectively, sulfobutylether derivatives of beta cyclodextrin and hydroxypropyl-beta-cyclodextrin with a degree of substitution of from about 4 to about 14, and combinations thereof.

Suitable peptides for use in the present invention include tribasic tripeptides and tribasic tetrapeptides, including but not limited to Peptide E (Arg-Ser-Arg-Lys), Peptide CK (Arg-Lys-Arg), Peptide CK+ (Ac-Arg-Lys-Arg-NH₂); the peptides His-Gly-Gly and Iamin, and combinations thereof. Peptide E (Arg-Ser-Arg-Lys), Peptide CK (Arg-Lys-Arg), Peptide CK+ (Ac-Arg-Lys-Arg-NH₂), His-Gly-Gly, Iamin and combinations thereof are preferred. Suitable tribasic tripeptides and tetrapeptides include those described in U.S. patent application Ser. No. 08/082,847, "Compositions For Regulating Wrinkles Comprising a Peptide" filed in the names of Andrew W. Fulmer and Charles C. Bascom on Jun. 25, 1993, allowed on Aug. 24, 1995, which is incorporated herein by reference.

Charged phospholipids that are suitable for use as the polar skin repair active include lysophosphatidic acid, 2-fluorolysophosphatidic acid, 2-deoxylysophosphatidic acid, and combinations thereof. Lysophosphatidic acid and 2-fluorolysophosphatidic acid are preferred. A detailed description of suitable charged phospholipids is provided in U.S. Pat. No. 5,340,568, issued to Mazur et al. on Aug. 23, 1994, incorporated herein by reference.

Additional polar skin repair actives that are suitable for use herein include sulfonated saccharides; phosphorylated saccharides; phosphorylated cyclodextrins; phosphonated saccharides; phosphonated cyclodextrins; polycarboxylate saccharides; and polycarboxylate cyclodextrins. Exemplary polycarboxylate cyclodextrins are succinylated beta-cyclodextrin and carboxymethyl beta-cyclodextrin. Currently preferred polar skin repair actives are the cyclic polyanionic polyols or derivatives having the structure described above. Preferred actives of this structure are those in which n is 1 or 2; X is $OSO_3^-$ or $OPO_3^{2-}$, all non-OH X's are the same, and the cation is $H^+$, $Na^+$, $K^+$, $NH_4^+$, $(HOCH_2CH_2)_3NH^+$, $HOCH_2(CH_3)_2CNH_3^+$, $(HOCH_2)CNH_3^+$, $CH_3(HOCH_2)_2CNH_3^+$, or a combination thereof. More preferred actives of this type are those in which n is 2, X is $OPO_3^{2-}$, all non-OH X's are the same, and the cation is $H^+$, $Na^+$, $K^+$, $NH_4^+$, $HOCH_2(CH_3)_2CNH_3^+$, $(HOCH_2)_3CNH_3^+$, $CH_3(HOCH_2)_2CNH_3^+$, or a combination thereof. Even more preferably, the cations is $Na^+$, $K^+$, and/or $NH_4^+$, with $Na^+$ being more preferred than $K^+$ which is more preferred than $NH_4^+$. Mixtures of $Na^+$ and $K^+$ are highly preferred. Where the cyclic polyanionic polyols are used as a skin repair active, it will generally be preferred to neutralize the composition to a pH of from 3 to 8, more preferably 5 to 7, such that $H^+$ will also be present.

Preferred cyclic polyanionic polyols for use herein include:

1,2,3,4,5,6-cyclohexanehexaphosphoric acid (scyllo, myo or other inositol hexakis phosphoric acid derivatives), having the structure:

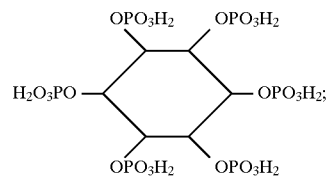

myo-inositol hexakisphosphate, calcium salt
myo-inositol hexakisphosphate, dimagnesium tetrapotassium salt
myo-inositol hexakisphosphate, magnesium potassium salt
myo-inositol hexakisphosphate, dipotassium salt
myo-inositol hexakisphosphate, monopotassium salt
myo-inositol hexakisphosphate, dodecasodium salt
myo-inositol hexakisphosphate, triethanolamine salt
myo-inositol hexakisphosphate, ammonium salt
myo-inositol hexakisphosphate, cetylpyridinium salt
myo-inositol hexakisphosphate, cetyltrimethylammonium salt
myo-inositol-1,3,4,5,6-pentakisphosphate, ammonium salt
myo-inositol-1,2,5,6-tetrakisphosphate, ammonium salt
myo-inositol-1,3,4,5-tetrakisphosphate, ammonium salt
myo-inositol-1,3,4,6-tetrakisphosphate, ammonium salt
myo-inositol-3,4,5,6-tetrakisphosphate, ammonium salt
myo-inositol-1,4,5-trisphosphate, potassium salt
myo-inositol-1,3,4-trisphosphate, ammonium salt myo-inositol-1,5,6-trisphosphate, ammonium salt
myo-inositol-2,4,5-trisphosphate, ammonium salt 1,2,3,4,5,6-cyclohexanchexasulfuric acid (scyllo, myo or other inositol hexakis sulfuric acid derivatives), having the structure:

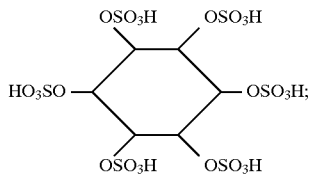

myo-inositol hexakissulfate, sodium salt
myo-inositol hexakissulfate, hexasodium salt
myo-inositol hexakissulfate, potassium salt
myo-inositol hexakissulfate, hexapotassium salt
myo-inositol hexakissulfate, ammonium salt
myo-inositol hexakissulfate, triethanolamine salt
myo-inositol hexakissulfate, cetylpyridinum salt
myo-inositol hexakissulfate, cetryltrimethylammonium salt
myo-inositol pentakissulfate, ammonium salt
myo-inositol tetrakissulfate, ammonium salt
myo-inositol trissulfate, potassium salt
myo-inositol-1,2,3-trissulfate-4,5,6-trisphosphate, sodium salt 1,2,3,4,5,6-cyclohexanehexaphosphonic acid, having the structure:

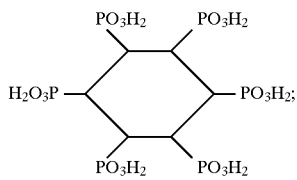

1,2,3,4,5,6-cyclohexanehexasulfonic acid, having the structure:

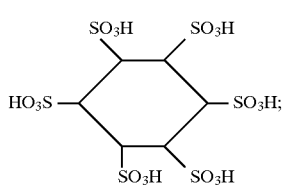

1,2,3,4,5,6-cyclohexanehexacarboxylic acid, having the structure:

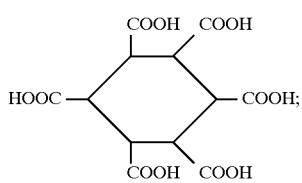

1,2,3,4,5-cyclopentanepentasulfuric acid, having the structure:

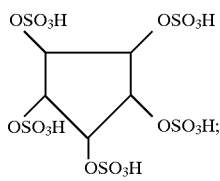

1,2,3,4,5-cyclopentanepentaphosphoric acid, having the structure:

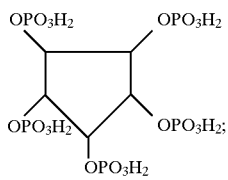

1,2,3,4,5,6,7-cycloheptaneheptasulfuric acid, having the structure:

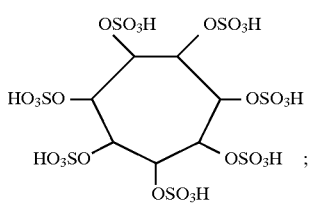

1,2,3,4,5,6,7-cycloheptaneheptaphosphoric acid, having the structure:

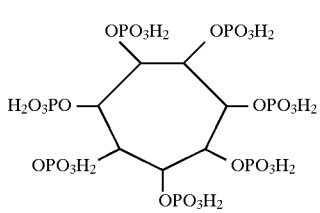

and the salts of the foregoing structures.

More preferred cyclic polyanionic polyols include myo-inositol hexakis phosphoric acid, myo-inositol hexakis sulfuric acid and myo-inositol 1,2,3 trissulfate—4,5,6-trisphosphate. Even more preferred cyclic polyanionic polyols include myo-inositol hexakis phosphoric acid and myo-inositol hexakis sulfuric acid. The more preferred cyclic polyanionic polyol is myo-inositol hexakis phosphoric acid.

Sulfhydryl Compound

The composition of this invention also comprise a sulfhydryl compound. As used herein "sulfhydryl compound" means a compound which contains an S-H group and which is capable of donating a hydrogen atom. The compositions may include one or more of the sulfhydryl compounds.

As well understood in the art, sulfhydryl compounds may exist in various derivative forms through tautomerism, di- or oligomerization through hydrogen bonds, hydration, or other spontaneous rearrangements, including the anionic S⁻ form. As used herein, "sulfhydryl compound" includes such other forms. If, in the sulfhydryl compounds useful in the invention, several mesomeric or tautomeric forms are conceivable, only one mesomeric or tautomeric form will be given for characterization, in accordance with conventional chemical nomenclature, with other forms intended to be embodied thereby. In general, the form as it naturally exists will be preferred.

As used herein, "sulfhydryl compound" includes the following derivatives of the sulfhydryl compounds: (i) cosmetically acceptable salts of the sulfhydryl compound and (ii) cosmetically acceptable hydrocarbyl esters of the sulfhydryl compound. The latter refers to carboxyl esters of those sulfhydryl compounds which also contain a carboxylic acid group with an alcohol consisting of a hydrocarbon with at least one hydroxyl group attached.

Cosmetically acceptable salts of the sulfhydryl compound include, but are not limited to alkali metal salts, e.g., sodium, lithium, potassium and rubidium salts; alkaline earth metal salts, e.g., magnesium, calcium and strontium salts; ammonium salts; trialkylammonium salts, e.g., trimethylammonium and triethylammonium; and tetralkylonium salts. Preferred cosmetically acceptable salts of the sulfhydryl compound include Na$^+$, K$^+$, Ca$^{++}$, Mg$^{++}$, Al$_2$(OH)$_5^+$, NH$_4^+$, (HOCH$_2$CH$_2$)$_3$NH$^+$, (CH$_3$CH$_2$)$_3$NH$^+$, (CH$_3$CH$_2$)$_4$N$^+$, C$_{12}$H$_{25}$(CH$_3$)$_3$N$^+$ and C$_{12}$H$_{25}$(C$_5$H$_4$N)$_3$N$^+$ salts. More preferred salts of the sulfhydryl compound include Na$^+$, K$^+$, NH$_4^+$, and (HOCH$_2$CH$_2$)$_3$NH$^+$ salts. Most preferred salts of the sulfhydryl compound include Na$^+$ and NH$_4^\infty$ salts. Suitable salts of the sulfhydryl compound are described, for example, in U.S. Pat. No. 5,296,500, issued to Hillebrand on Mar. 22, 1994, incorporated herein by reference.

Cosmetically acceptable hydrocarbyl esters of sulfhydryl compounds include carboxyl esters of the sulfhydryl compound with primary, secondary, and tertiary aliphatic alcohols containing from 1 to about 24 carbon atoms, unsaturated primary alcohols containing from about 10 to about 24 carbon atoms, and aryl and alkylaryl alcohols containing one or more aromatic rings. Examples of suitable alcohols include but are not limited to: methanol, ethanol, n-propanol, isopropanol, n-butanol, isobutanol, sec-butanol, n-pentanol, n-hexanol, n-heptanol, n-octanol, 2-ethylhexanol, n-decanol, lauryl alcohol, myristyl alcohol, palmityl alcohol, stearyl alcohol, olelyl alcohol, linoleyl alcohol, linolenyl alcohol, behenyl alcohol, cyclohexanol, and benzyl alcohol. Preferred alcohols are ethanol, n-propanol, ispropanol, n-butanol, isobutanol, sec-butanol, 2-ethylhexanol, lauryl alcohol, myristyl alcohol, stearyl alcohol, oleyl alcohol, and benzyl alcohol. Most preferred are ethanol, isopropanol, sec-butanol, and benzyl alcohol.

Exemplary sulfhydryl compounds include N-acetylcysteine, cysteine, glutahlione, thioglycolic acid, thioglycolic acid ethyl ester, thiosalicylic acid, cysteamine, dithiothreitol, lipoic acid, dithioerythritol, thioacetic acid, thiolactic acid, mercaptoethanol, dimercaptol, monothloglycerol, N-(2-mercaptoproprionyl)glycine, bucillamine, mercaptomenthone, and cosmetically acceptable derivatives thereof. Preferred sulfhydryl compounds are selected from the group consisting of:

a) N-acetyl-L-cysteine, having the structure:

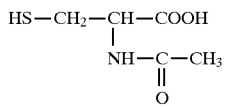

b) glutathione, having the structure:

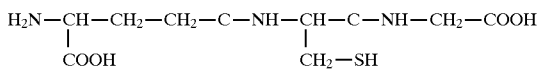

c) dithiothreitol, having the structure:

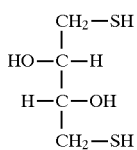

d) dithioerythritol, having the structure:

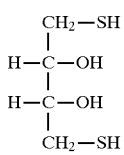

e) cysteine, having the structure:

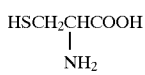

f) thioglycolic acid;
g) thioglycolic acid ethyl ester;
h) thiosalicylic acid (2-mercaptobenzoic acid);
i) cysteamine;
j) lipoic acid; and
j) cosmetically acceptable derivatives of the foregoing compounds.

While the aforementioned, preferred sulfhydryl compounds are shown in their protonated forms, it is meant to include the other forms of these compounds which are known to exist.

More preferred sulfhydryl compounds useful in the subject invention include N-acetylcysteine (especially the D and L isomers), cysteine (especially the D and L isomers), glutathione, dithiothreitol, dithioerythritol, and cosmetically acceptable derivatives of the foregoing compounds. The most preferred sulfhydryl compound is N-acetyl-L-cysteine or a cosmetically acceptable derivative thereof.

Zwitterionic Surfactant

The compositions of the present invention also contain a zwitterionic surfactant. Suitable zwitterionic surfactants include long chain (preferably C$_9$–C$_{22}$) betaines and sultaines.

As used herein, "zwitterionic surfactant" includes cosmetically acceptable salts of the zwitterionic surfactants described herein. Preferred cosmetically acceptable salts include alkali metal salts, alkaline earth metal salts, non-toxic heavy metal salts, boron salts, silicon salts, ammonium salts, trialkylammonium salts, and tetralkylammonium salts such as described hereinabove in reference to the sulfhydryl compound.

Preferred zwitterionic surfactants are those having the structure:

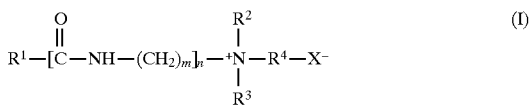

In structure (I) R$^1$ is unsubstituted, saturated or unsaturated, straight or branched chain alkyl having from about 9 to about 22 carbon atoms. Preferred R$^1$ has from about 11 to about 18 carbon atoms; more preferably from about 12 to about 16 carbon atoms; more preferably still from about 14 to about 16 carbon atoms.

In structure (I), m is an integer from 1 to 3, preferably 2 or 3; more preferably 3.

In structure (I), n is either 0 or 1; n is preferably 0.

In structure (I), $R^2$ and $R^3$ are, independently, selected from the group consisting of alkyl having from 1 to about 3 carbon atoms, unsubstituted or mono-substituted with hydroxy. Preferred $R^2$ and $R^3$ are $CH_3$.

In structure (I), X is selected from the group consisting of $CO_2$, $SO_3$ and $SO_4$.

In structure (I), $R^4$ is selected from the group consisting of saturated or unsaturated, straight or branched chain alkyl, unsubstituted or mono-substituted with hydroxy, having from 1 to about 5 carbon atoms. When $X=CO_2$, $R^4$ preferably has 1 or 3 carbon atoms, more preferably 1 carbon atom. When $X=SO_3$ or $SO_4$, $R^4$ preferably has from about 2 to about 4 carbon atoms, more preferably 3 carbon atoms.

Preferred zwitterionic surfactants of the subject invention include the following compounds:

a) cetyl betaine, having the structure:

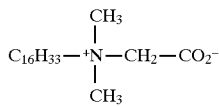

b) stearyl betaine, having the structure:

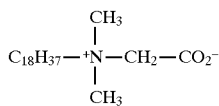

c) cocoamidopropylbetaine, having the structure:

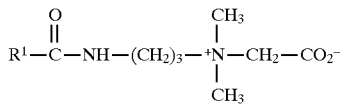

wherein $R^1$ is unsubstituted, saturated, straight chained alkyl with from about 9 to about 13 carbon atoms;

d) cetyl propyl hydroxy sultaine, having the structure:

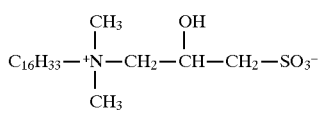

e) cocoamidopropyl hydroxy sultaine, having the structure:

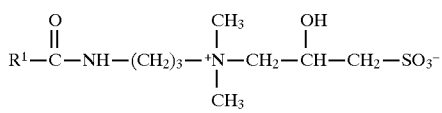

wherein $R^1$ has from about 9 to about 13 carbon atoms; and f) behenyl betaine, having the structure:

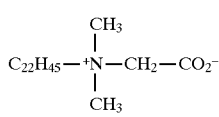

One or more zwitterionic surfactants may be used in the present invention. More preferred zwitterionic surfactants of the subject invention include cetyl betaine, stearyl betaine, cocoamidopropyl betaine, cetyl propyl hydroxy sultaine or mixtures thereof. Still more preferred zwitterionic surfactants of the subject invention include cetyl betaine, stearyl betaine, cocoamidopropyl betaine or mixtures thereof. The zwitterionic surfactant is even more preferably cetyl betaine and/or stearyl betaine. The most preferred zwitterionic surfactant of the subject invention is cetyl betaine.

Preferred Compositions

The compositions of the present invention comprise at least one of each of the polar skin repair actives, sulfhydryl compounds, and zwitterionic surfactants according to structure (I) described herein above in safe and effective amounts. The compositions preferably comprise from about 0.01% to about 10% of polar skin repair active, from about 0.1% to about 20% of sulfhydryl compound, and from about 0.1% to about 10% of zwitterionic surfactant according to structure (I). More preferred compositions comprise from about 0.05% to about 5% of polar skin repair active, from about 0.2% to about 10% of sulfhydryl compound, and from about 0.2% to about 5% of said zwitterionic surfactant. Most preferred compositions comprise from about 0.1% to about 5% of polar skin repair active, from about 0.5% to about 5% of sulfhydryl compound, and from about 0.5% to about 2% of said zwitterionic surfactant.

Cosmetically Acceptable Carrier

The phrase "cosmetically acceptable carrier", as used herein, means one or more compatible solid or liquid fillers, diluents, extenders and the like, which are cosmetically acceptable as defined herein. The term "compatible", as used herein, means that the components of the compositions of this invention are capable of being comingled with the primary actives of the present invention, and with each other, in a manner such that there is no interaction which would substantially reduce the efficacy of the composition under ordinary use situations. The type of carrier utilized in the present invention depends of the type of product desired. The topical compositions useful in the subject invention may be made into a wide variety of product types. These include, but are not limited to, lotions, creams, gels, sticks, sprays, ointments, pastes, mousses and cosmetics (e.g., solid, semi-solid, liquid make-up, including foundations). These product types may comprise several types of carriers including, but not limited to solutions, aerosols, emulsions (including water-in-oil and oil-in-water), gels, solids, and liposomes.

Solutions according to the subject invention typically include a cosmetically acceptable aqueous or organic solvent which is capable of having the primary actives dispersed or dissolved therein. Water is a preferred solvent. Examples of suitable organic solvents include: propylene glycol, polyethylene glycol (e.g., Molecular Weight 200–600 g/mole), polypropylene glycol (e.g., Molecular Weight 425–2025 g/mole), glycerol, 1,2,4-butanetriol, sorbitol esters, 1,2,6-hexanetriol, ethanol, isopropanol, sorbitol esters, butanediol, and mixtures thereof. Solutions useful in the subject invention preferably contain from about 80% to about 99.99% of an acceptable aqueous or organic solvent and the primary actives in the above described amounts.

Aerosols according to the subject invention can be formed by adding a propellant to a solution such as described above. Exemplary propellants include chloro-fluorinated lower molecular weight hydrocarbons. Additional propellants that are useful herein are described in Sagarin, *Cosmetics Science and Technology*, 2nd Edition, Vol. 2, pp. 443–465 (1972), incorporated herein by reference. Aerosols are typically applied to the skin as a spray-on product.

Emulsions according to the present invention generally contain a solution as described above and a lipid or oil.

Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are disclosed in, for example, U.S. Pat. No. 3,755,560, issued Aug. 28, 1973, Dickert et al., U.S. Pat. No. 4,421,769, issued Dec. 20, 1983, Dixon et al.; and *McCutcheon's Detergents and Emulsifiers,* North American Edition, pages 317–324 (1986), each incorporated herein by reference.

The emulsion may also contain an anti-foaming agent to minimize foaming upon application to he skin. Anti-foaming agents include high molecular weight silicones and other materials well known in the art for such use.

The emulsions preferably comprise a silicone for imparting a preferred skin feel. Generally such silicones have a low molecular weight. Suitable such silicones include cyclomethicones, dimethicones, and blends such as Dow Corning 200 fluid (especially 10 cs) and Dow Corning Q2-1401. Such silicones are commercially available from the Dow Corning Corp. of Midland, Mich.

Preferred emulsions have a high viscosity, of from about 10,000 to about 300,000 centipoise, more preferably from about 20,000 to about 200,000 centipoise, most preferably from about 50,000 to about 150,000 centipoise.

The topical compositions of the subject invention may comprise a topical cosmetically acceptable emollient. Such compositions preferably contain from about 2% to about 50% of the emollient. As used herein, "emollient" refers to a material used for the prevention or relief of dryness, as well as for the protection of the skin. A wide variety of suitable emollients are known and may be used herein. Segarin, *Cosmetics Science and Technology,* 2nd Edition, Vol. 1, pp. 32–43 (1972), incorporated herein by reference, contains numerous examples of materials suitable as an emollient.

Lotions and creams according to the present invention generally comprise a solution carrier system and one or more emollients. Lotions typically comprise from about 1% to about 20%, preferably from about 5% to about 10%, of emollient; from about 50% to about 90%, preferably from about 60% to about 80% water, and the primary actives in the above described amounts. A cream typically comprises from about 5% to about 50%, preferably from about 10% to about 20%, of emollient, from about 45% to about 85%, preferably from about 50% to about 75% water, and the primary actives in the above described amounts.

In addition to the primary actives, ointments of the present invention may comprise a simple carrier base of animal or vegetable oils or semi-solid hydrocarbons (oleginous), absorption ointment bases which absorb water to form emulsion, or water soluble carriers, e.g., a water soluble solution carrier. Ointments may further comprise a thickening agent, such as described in Sagarin, *Cosmetics Science and Technology,* 2nd Edition, Vol. 1, pp. 72–73 (1972), incorporated here by reference, and/or an emollient. For example, an ointment may comprise from about 2% to about 10% of an emollient; from about 0.1% to about 2% of a thickening agent; and the primary actives in the above described amount.

Compositions of this invention useful for cleansing ("cleansers") are formulated with a suitable carrier, e.g., as described above, and preferably contain, in addition the primary actives in the above described amounts, from about 1% to about 90%, more preferably from about 5% to about 10%, of a cosmetically acceptable surfactant. The surfactant is suitably selected from anionic, nonionic, zwitterionic, amphoteric and ampholytic surfactants, as well as mixtures of these surfactants. Such surfactants are well known to those skilled in the detergency art and are generally selected for their detergency action, mildness to the skin, and compatibility with the primary actives. Nonlimiting examples of suitable surfactants include isoceteth-20, sodium methyl cocoyl taurate, sodium methyl oleoyl taurate, and sodium lauryl sulfate. See U.S. Pat. No. 4,800,197, to Kowcz et al., issued Jan. 24, 1989, which is incorporated herein by reference in its entirety, for exemplary surfactants useful herein. Examples of a broad variety of additional surfactants useful herein are described in *McCutcheon's Detergents and Emulsifiers,* North American Edition (1986), published by Allured Publishing Corporation, which is incorporated herein by reference in its entirety. The cleansing compositions can optionally contain, at their art-established levels, materials which are conventionally used in cleansing compositions.

The physical form of the cleansing compositions is not critical. The compositions can be, for example, formulated as toilet bars, liquids, shampoos, pastes, or mousses. Toilet bars are most preferred since this is the form of cleansing agent most commonly used to wash the skin. Rinse-off cleansing compositions, such as shampoos, require a delivery system adequate to deposit sufficient levels of actives on the skin or scalp. A preferred delivery system involves the use of insoluble complexes. For a more complete disclosure of such delivery systems, see U.S. Pat. No. 4,835,148, Barford et al., issued May 30, 1989, incorporated herein by reference in its entirety.

The compositions of the present invention are preferably formulated to have a pH of 8.5 or below. The pH values of these compositions preferably range from about 2 to about 8.5, more preferably from about 3 to about 7, most preferably from about 4.5 to about 5.5. Compositions have a pH within the range of about 4.5 to 7 tend to exhibit less skin irritation, less odor, and greater shelf stability relative to corresponding compositions having a pH of greater than about 8.5. Preferred emulsions of the invention are formulated at intermediate pH values, preferably from about 3 to about 7, more preferably about 4.5 to about 5.5.

Optional Ingredients

The compositions of this invention may contain other ingredients, including but not limited to preservatives, preservative enhancers, and actives in addition to the primary actives. Any optional ingredients should be compatible with the primary active agents such that the activity of the primary actives does not decrease unacceptably, preferably not to any significant extent, over a useful period (preferably at least one year, more preferably at least two years, under normal storage conditions).

Preferred compositions contain a preservative, preservative enhancer, zinc, and/or a zinc salt as described herein. These agents may be incorporated into the aforementioned formulations in the amounts described herein.

For example, certain agents may decrease the activity of the sulfhydryl compound, particularly N-acetyl-L-cysteine, over time. First, an excessive number of microbes may decrease the activity of the sulfhydryl compound, for example by microbial metabolism of the compound. Second, it has been found that formaldehyde can chemically react with the sulfhydryl compound to decrease its activity. Thus, when a composition containing the sulfhydryl compound is formulated with formaldehyde or a formaldehyde forming preservative or other material, the composition may have decreased activity of the sulfhydryl compound over time relative to the corresponding formulation that does not contain formaldehyde or a compound capable of forming formaldehyde. Therefore, it is desirable to provide compositions containing sulfhydryl compounds that are resistant to microbial contamination and which do not include formaldehyde or formaldehyde forming preservatives or other materials.

The compositions of this invention are therefore preferably substantially free of formaldehyde and materials that may form or release formaldehyde when present in the composition, including preservatives that may form or release formaldehyde in the composition. Formaldehyde and materials that may form or release formaldehyde in the composition are alternatively referred to herein as "formaldehyde donor(s)." As used herein, "substantially free of formaldehyde donors" means that there are no detectable formaldehyde donors, preferably no formaldehyde donors. The presence of formaldehyde donors may be indicated by the presence of formaldehyde in the composition by any suitable analytical technique, for example high pressure liquid chromatography (HPLC). The presence of such donors may be detected initially or evidenced by the generation of formaldehyde over time. Preferred compositions are those which evidence no formaldehyde upon storage over a period of at least 2 months at 45° C., when measured using a sensitive analytical method such as HPLC.

Preservatives

The topical compositions of the invention preferably comprise one or more preservatives. Preferred preservatives are those which are substantially free of formaldehyde donors. Thus, the preservatives preferred for use herein are those that do not form or release formaldehyde in the composition either in the process of preserving or in an unrelated process. In contrast, formaldehyde forming or releasing preservatives form or release formaldehyde in the composition either in the process of preserving or in an unrelated process.

Most preferred preservatives include benzyl alcohol, propylparaben, ethylparaben, butylparaben, methylparaben, benzylparaben, isobutylparaben, phenoxyethanol, ethanol, sorbic acid, benzoic acid, methylchloroisothiazolinone, methylisothiazolinone (a preservative containing a mixture of methylchloroisothiazolinone and methylisothiazolinone being commercially available, for example, from Rohm & Haas as Kathon CG®), methyl dibromoglutaronitrile (commercially available, for example, from Calgon as Tektamer 38®), dehydroacetic acid, o-phenylphenol, sodium bisulfite, dichlorophen, salts of any of the foregoing compounds, and mixtures of any of the foregoing compounds.

Even more preferred preservatives are selected from the group consisting of benzyl alcohol, propylparaben, methylparaben, phenoxyethanol, methylchloroisothiazolinone, methylisothiazolinone, benzoic acid, salts of any of the foregoing preservatives, and mixtures of any of the foregoing compounds.

Still more preferred preservatives are benzyl alcohol, propylparaben, methylparaben, phenoxyethanol and mixtures thereof. Yet even more preferably, the preservative is a mixture of propylparaben and methyl paraben with either or both of benzyl alcohol and phenoxyethanol. In addition to stability of the sulfhydryl compound, these mixtures provide broad preservative efficacy with no or only minimal risk of skin irritation to the user. Most preferably, the preservative is a mixture of benzyl alcohol, propylparaben and methylparaben. In addition to stability of the sulfhydryl compound and broad preservative efficacy, this mixture presents a particularly low risk of skin irritation to the user.

The use of the foregoing preservatives that are substantially free of formaldehyde donors is described in more detail in the copending U.S. patent application Ser. No. 08/479,879, entitled "Topical Compositions Comprising N-Acetyl-L-Cysteine," filed on Jun. 7, 1995 in the names of Greg G. Hillebrand and Marcia S. Schnicker, which is incorporated herein by reference in its entirety. The foregoing preservatives are preferably used in the compositions of this invention in the same amounts as described for the compositions of the just referenced patent application.

Preservative Enhancer

The compositions of this invention containing a preservative also preferably comprise a safe and effective amount of a preservative enhancer. As used here, "preservative enhancer" means an agent whose purpose is to enhance the activity of the preservative. As will be understood by the artisan having ordinary skill, the preservative enhancer does not itself typically provide a level of preservative efficacy preferred for commercial products; rather it tends to increase the efficacy of the preservative. Enhancement of the preservative efficacy may involve chelation. Preferred preservative enhancers useful in the present invention include ethylenediaminetetraacetic acid (EDTA), butylene glycol, propylene glcol, ethanol, and mixtures thereof. Where the preservative includes a paraben, e.g., methyl or propyl paraben, EDTA is the preferred preservative enhancer. The use of such enhancers is described in more detail in the above-referenced and incorporated copending U.S. patent application Ser. No. 08/479,879. The preservative enhancers are preferably used in the compositions of this invention in the amounts described for the compositions of the patent application Ser. No. 08/479,879. For example, a currently preferred composition comprises about 0.3% EDTA, based on the weight of the composition.

Zinc Compound

The compositions of the invention preferably contain zinc or a zinc salt which may complex with the sulfhydryl compound. Without intending to be bound or limited by theory, the zinc most likely removes odor by complexing with malodorous $H_2S$ which may be formed in trace amounts as the sulfhydryl compound decomposes. The zinc may additionally or alternatively increase the stability of the sulfhydryl compound. The use of zinc salts in a manner which is suitable for the present invention is further described in U.S. Pat. No. 5,296,600, Hillebrand, issued on Mar. 22, 1994, which is incorporated herein by reference. Preferred zinc salts are zinc oxide and zinc citrate.

Thickeners

The zwitterionic surfactant tends to decrease the viscosity of the composition. Therefore, a thickener may be employed in the compositions of the invention to thicken the composition and/or to minimize the risk of phase separation. Exemplary thickeners include cetyl hydroxyethylcellulose (e.g., Natrosol Plus 330, commercially available from Aqualon of Wilmington, Del.) and those thickeners commercially available under the trade name SALCARE from Allied Colloids of Bradford, England. A preferred thickener is SALCARE 95, which is a mixture of polyquaternium-37 (a polymeric quaternary amine), mineral oil and PPG-1 trideceth-6 (polyoxypropylene/polyoxyethylene ether of tridecyl alcohol generally having the formula $C_{13}H_{27}$ $(OCHCH_3CH_2)_x(CH_2CH_2)_yOH$, where x is 1 and y is 6). The thickener should be compatible with the components of the composition or otherwise be employed in relatively low levels so as to not significantly decrease the efficacy of the zwitterionic surfactant over a useful commercial period. Typically, about 0.1 to about 0.5% thickener is employed.

Other Actives

The compositions of the subject invention may optionally comprise other actives capable of functioning in different ways to enhance the benefits of the primary actives and/or to provide other benefits. Examples of such substances include, but are not limited to anti-inflammatory agents, antimicrobial agents, anti-androgens, sunscreens, sunblocks, anti-oxidants/radical scavengers, chelators, anti-dandruff agents, organic hydroxy acids, light diffusion agents, and pigments.

A. Anti-Inflammatory Agents

A safe and effective amount of an anti-inflammatory agent may be added to the compositions useful in the subject invention, preferably from about 0.1% to about 10%, more preferably from about 0.5% to about 5%, of the composition. The anti-inflammatory agent enhances the skin appearance benefits of the present invention, e.g., such agents contribute to a more uniform and acceptable skin tone. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludocortisone, flumethasone privalate, fluocinolone acetonide, fluocinonide, flucortine butylesters, fluocotolone, fluprednidene (fluprednylidene) acetate, flurandrenolone, halcinonide, hydrocortisone acetate, hydrocortisone butyrate, methylprednisolone, tramcinolone acetonide, cortisone, cortodoxone, fluctonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clorotelone, clescinolone, dichlorisone, difluprednate, flucloronide, flunisolide, floromethalone, fluperolone, fluprednisolone, hydrocortisone valerate, hydrocortisone cyclopentylpropionate, hydrocortamate, meprednisone, paramethasone, prednisolone, prednisone, beciomethasone dipropionate, trimcinolone, and mixtures thereof may be used. The preferred steroidal anti-inflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc. of non-steroidal anti-inflammatory agents, reference may be had to standard texts, including *Anti-inflammatory and Anti-Rheumatic Drugs*, K. D. Rainsford, Vol. I–III, CRC Press, Boca Raton, (1985), and *Anti-inflammatory Agents, Chemistry and Pharmacology*, 1, R. A. Scherrer, et al., Academic Press, N.Y. (1974), each incorporated herein by reference.

Specific non-steroidal anti-inflammatory agents useful in the composition invention include, but are not limited to:
1) the oxicams, such as piroxicam, isoxicam, tenoxicam, sudoxicam, and CP-14,304;
2) the salicylates, such as aspirin, disalcid, benorylate, trilisate, safapryn, solprin, diflunisal, and fendosal;
3) the acetic acid derivatives, such as diclofenac, fenclofenac, indomethacin, sulindac, tometin, isoxepac, furofenac, tiopinac, zidometacin, acematacin, fentiazac, zomepirac, clindanac, oxepinac, felbinac, and ketorolac;
4) the fenamates, such as mefanamic, meclofenamic, flufenamic, niflumic, and tolfenamic acids;
5) the propionic acid derivatives, such as ibuprofen, naproxen, benoxaprofen, flurbiprofen, ketoprofen, fenoprofen, fenbufen, indopropfen, piroprofen, carprofen, oxaprozin, pranoprofen, microprofen, tioxaprofen, suprofen, alminoprofen, and tiaprofenic; and
6) the pyrazoles, such as phenylbutazone, oxyphenbutazone, feprazone, azapropazone, and trimethazone.

Mixtures of these non-steroidal anti-inflammatory agents may also be employed, as well as the cosmetically acceptable salts and esters of these agents. For example, etofenamate, a flufenamic acid derivative, is particularly useful for topical application. Of the nonsteroidal anti-inflammatory agents, ibuprofen, naproxen, flufenamic acid, mefenamic acid, meclofenamic acid, piroxicam and felbinac are preferred; ibuprofen, naproxen, and flufenamic acid are most preferred.

Finally, so-called "natural" anti-inflammatory agents are useful in methods of the subject invention. For example, candelilla wax, alpha bisabolol, aloe vera, Manjistha (extracted from plants in the genus Rubia, particularly *Rubia Cordifolia*), and Guggal (extracted from pants in the genus Commiphora, particulary *Commiphora Mukul*), may be used.

B. Retinoids

A safe and effective amount of a retinoid may be added to the compositions of the subject invention, preferably from about 0.001% to about 0.5%, more preferably from about 0.01% to about 0.1% of the composition. As used herein, "retinoid" includes all natural and/or synthetic analogs of Vitamin A or retinol-like compounds which possess the biological activity of Vitamin A in the skin as well as the geometric isomers and steroisomers of these compounds, such as all-trans retinoic acid and 13-cis-retinoic acid. The retinoid is preferably retinol, retinal, or retinoic acid, more preferably retinol.

The retinoids enhance the skin appearance benefits of the present invention. For example, the retinoids may diminish fine lines, wrinkles, other textural discontinuities, or skin color discontinuities.

C. Antimicrobial Agents

As used herein, "antimicrobial agent" means a compound capable of destroying microbes, preventing the development of microbes or preventing the pathogenic action of microbes. The antimicrobial agent enhances the skin appearance benefits of the present invention. A safe and effective amount of an antimicrobial agent may be added to compositions of the subject invention, preferably from about 0.001% to abut 10%, more preferably from about 0.01% to about 5%, also from about 0.05% to about 1% or 2% of the compositions. Preferred antimicrobial agents useful in the subject invention are benzoyl peroxide, erythromycin, tetracycline, clindamycin, azelaic acid, and sulfur resorcinol.

D. Antiandrogens

As used herein, "anti-androgen" means a compound capable of correcting androgen-related disorders by interfering with the action of androgens at their target organs. The target organ for the subject invention is mammalian skin.

E. Sunscreens and Sunblocks

Exposure to ultraviolet light can result in excessive scaling, texture changes and other changes of the stratum corneum. Therefore, the compositions of the subject invention preferably contain a sunscreen or sunblock to enhance the skin appearance benefits of the invention. The sunscreens/sunblocks tend to provide photoprotection, thus preventing, retarding or arresting sunlight ultraviolet radiation-induced damage to the skin, such as sunburn, blistering, peeling skin wrinkling, skin cancer, agent spots, irregular pigmentation, rough texture, and dryness. Suitable sunscreens or sunblocks may be organic or inorganic.

A wide variety of conventional sunscreening agents are suitable for use herein. Sagarin, et al., at Chapter VIII, pages 189 et seq., of *Cosmetics Science and Technology* (1972), discloses numerous suitable agents, and is incorporated herein by reference. Specific suitable sunscreening agents include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-propyleneglycol esters); Cinnamic acid derivatives (menthyl and benzyl esters, a-phenyl cinnamonitrile; butyl cinnamoyl pyruvate); dihydroxycinnamic acid derivatives (umbeliferone, methylumbelliferone, methylacetoumbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphtol-3,6-disulfonic and of 2-naphthol-6,8-disulfonic acids); di-hydroxynaphthoic acid and its salts; o- and p-Hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, olcate, and tannate); quinoline derivatives (8-hydroxyquinoline salts, 2-phenylquinoline); hydroxy- or methoxy-substituted benzophenones; uric and vilouric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; [3-(4'-methylbenzylidene bornan-2-one) and 4-isopropyl-di-benzoylmethane.

Of these, 2-ethylhexyl-p-methoxycinnamate, 4,4'-t-butyl methoxydibenzoyl-methane, 2-hydroxy-4-methoxybenzophenone, octyldimethyl-p-aminobenzoic acid, digalloyltrioleaic, 2,2-dihydroxy-4-methoxybenzophenone, ethyl-4-(bis(hydroxy-propyl)) aminobenzoate, 2-ethylhexyl-2-cyano-3,3-diphenylacrylate, 2-ethylhexyl-salicylate, glyceryl-p-aminobenzoate, 3,3,5-tir-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid and mixtures of these compounds, are preferred.

Most preferred sunscreens useful in the compositions useful in the subject invention are 2-ethylhexyl-p-methoxycinnamate, butylmethoxydibenzoylmethan, 2-hydroxy-4-methoxybenzophenone, octyldimethyl-p-aminobenzoic acid and mixtures thereof.

Also particularly useful in the compositions are sunscreens such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991, both of which are incorporated herein by reference. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methylaminobenzoic acid ester with 4-hydroxydibenzoylmethane; 4-N,N-(2-ethylhexyl) methylaminobenzoic acid ester of 2-hydroxy-4-(2-hydroxyethoxy)dibenzoylmethane; N,N-do-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy) dibenzoylmethane and mixtures thereof.

Suitable inorganic sunscreens or sunblocks include metal oxides, e.g., zinc oxide and titanium dioxide. For example, the sue of titanium dioxide in topical sunscreen compositions that is applicable to the present invention is described in copending application Ser. No. 08/448,942, filed on May 24, 1995, in the names of Jiang Yue, Lisa R. Dew and Donald L. Bissett, incorporated herein by reference.

A safe and effective amount of the sunscreen or sunblock is used, typically from about 1% to about 20%, more typically from about 2% to about 10%. Exact amounts will vary depending upon the sunscreen chosen and the desired Sun Protection Factor (SPF).

An agent may also be added to any of the compositions useful in the subject invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

F. Anti-Oxidants/Radical Scavengers

While the sulfhydryl compound (e.g., glutahione) may itself impart anti-oxidant properties to the composition, preferred compositions of the subject invention include an anti-oxidant/radical scavenger as an active in addition to the primary active agents. The anti-oxidant/radical scavenger enhances the skin appearance benefits of the present invention. For example, such agents provide protection against radiation which can cause increased scaling, texture changes or other changes in the stratum corneum and against other environmental agents which can cause skin damage. Anti-oxidants/radical scavengers tend to prevent, retard or arrest the damaging effects of oxygen radicals, whether arising from the environment (such as smoke, pollution, or ultra-violet radiation exposure) or from endogenous sources (such as products from normal metabolism), on the skin. Such damage includes sunburn, blistering, peeling, skin wrinkling, skin cancer, skin sagging, skin yellowing, age spots, irregular pigmentation, rough texture, and dryness.

A safe and effective amount of an anti-oxidant/radical scavenger may be added to the compositions of the subject invention, preferably from about 0.1% to about 10%, more preferably from about 1% to about 5%, of the composition.

Anti-oxidants/radical scavengers such as ascorbic acid (vitamin C) and it salts, tocopherol (vitamin E), tocopherol sorbate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, aminoguanidine), dihydroxy fumaric acid and its salts, green tea polyphenols, and proanthrocyanidine (commercially available as PYCNOGENOL from M. W. International, Inc. of West Hillside, N.J.) may be used. Preferred anti-oxidants/radical scavengers are selected from tocopherol sorbate, and esters of tocopherol, and PYCNOGENOL, most preferably the antioxidant is tocopherol sorbate. For example, the use of tocopherol sorbate in topical compositions and applicable to the present invention is described in U.S. Pat. No. 4,847,071, issued on Jul. 11, 1989 to Donald L. Bissett, Rodney D. Bush and Ranjit Chatterjee, incorporated herein by reference.

G. Chelators

As used herein, "chelating agent" means an active agent capable of removing a metal ion from a system by forming a complex so that the metal ion cannot readily participate in or catalyze chemical reactions. The chelating agent enhances the skin appearance benefits of the present invention. The chelating agent tends to be particularly effective in providing photoprotection. For example, the chelating agent provides protection against UV radiation which can contribute to excessive scaling or skin texture changes and against other environmental agents which can cause skin damage.

A safe and effective amount of a chelating agent may be added to the compositions of the subject invention, preferably from about 0.1% to about 10%, more preferably from about 1% to about 5%, of the composition. Chelators useful herein are disclosed in U.S. patent application Ser. No. 619,805, Bissett, Bjush & Chatterjee, filed Nov. 27, 1990 (which is a continuation of U.S. patent application Ser. No. 251,910, filed Oct. 4, 1988); U.S. patent application Ser. No. 514,892, Bush & Bissett, filed Apr. 26, 1990; and U.S. patent application Ser. No. 657,847, Bush, Bissett & Chatterjee, filed Feb. 25, 1991; all incorporated herein by reference. Preferred chelators useful in compositions of the subject invention are furldioxime, Octopirox (commercially available from Hoeschst of Germany), furilmonoxime, chelator L1 (1,2-dimethyl-3-hydroxy-pyrid-4-one), deferoxamine (commercially available as DESFERAL from Ciba-Geigy of Aardsley, N.Y.), and derivative thereof. More preferred chelators are furildioxime, furilmonoxime, chelator L1 and deferoxamine, most preferred chelators are furildioxime, chelator L1 and deferoxamine.

H. Anti-dandruff Actives

An anti-dandruff agent may be included in compositions of the present invention that are intended for application to the scalp. Anti-dandruff agents prevent and treat the effects of flaking on the scalp. A particularly preferred anti-dandruff agent is zinc pyridinethione.

I. Organic Hydroxy Acids

The compositions of the present invention preferably comprise from about 0.1% to about 10%, more preferably from about 0.2% to about 5%, also preferably from about 0.5% to about 2%, of an organic hydroxy acid such as salicylic acid, glycolic acid, or lactic acid. Salicylic acid is preferred. The organic hydroxy acids enhance the skin appearance benefits of the present invention. For example, the organic hydroxy acids tend to improve the texture of the skin.

J. Other Combination Actives

The compositions of the present invention may also include a natural extract of yeast, rice bran, or other natural extracts such as are known in the art. Such extracts enhance the skin appearance benefits of the present invention, and are preferably used in an amount of from 0.1% to about 20%, more preferably 0.5% to about 10%, also from 1% to about 5%. A natural extract of yeast is preferred.

The compositions may also comprise a vitamin B (including but not limited to niacin, niacinamide, pyridoxine or mixtures thereof) or vitamin B complex.

K Light Diffusion Agents and Pigments

The compositions of the present invention may also include finely divided particulate solids that scatter, diffuse, or absorb light. Such ingredients when used as appropriate levels may enhance the skin appearance benefits of the present invention, and are preferably used in a an amount of from 0.01% to about 20%, more preferably from about 0.05% to about 5%, also from about 0.1% to about 1%. A preferred light diffusion agent is titanium dioxide. An exemplary pigment is red iron oxide ($Fe_2O_3$). Additional pigments suitable for use with the present invention are described in Harry's Cosmetology, 7th Ed. (Wilkinson and Moore, Eds.), Chemical Publishing Co., N.Y. (1982), incorporated herein by reference.

Preparation of Compositions

The compositions of the present invention are generally prepared by conventional methods such as are known in the art of making topical compositions. Such methods typically involve mixing of the ingredients to a relatively uniform state, with or without heating, cooling, application of vacuum, and the like. Exemplary methods are described in Remington's Pharmaceutical Sciences, 17th Ed. (A. R. Gennaro, Ed.), Mack Publishing Company, Easton Pa., 1985, pp. 301–329, 1492–1517, incorporated herein by reference. For optimum stability of the sulfhydryl compound, the compositions of this invention should be manufactured, packaged and stored in a manner which avoids simple air oxidation of the sulfhydryl compound. Thus, exposure of the compositions to air during manufacture, packaging and storage should be minimized. Techniques for minimizing such exposure are well known in the art, and include, e.g., the use of inert gas atmospheres or vacuum conditions.

Delivery Methods for the Topical Compositions

The topical compositions useful for the method of the instant invention can be delivered from a variety of delivery devices. The following are three nonlimiting examples.

A. Application Pads

The compositions useful herein can be incorporated into an application pad, e.g., a cleansing pad. Preferably these application pads comprise from about 50% to about 75% by weight of one or more layers of nonwoven fabric material and from about 20% to about 50% by weight of a liquid composition of the present invention deliverable from the nonwoven fabric material. Pads useful in the present invention are described in detail in U.S. Pat. No. 4,891,228, to Thaman et al., issued Jan. 2, 1990; and U.S. Pat. No. 4,891,227, Thaman et al., issued Jan. 2, 1990; both of which are incorporated by reference herein in their entirety.

B. Dispensing Devices

The compositions of the present invention can also be incorporated into an delivered from a dispensing device, e.g., a soft-tipped or flexible dispensing device. Such devices are useful for the controlled delivery of the compositions to the skin surface and have the advantage that the composition itself never need be directly handled by the user. Nonlimiting examples of these devices include a fluid container having a mouth, an applicator, means for holding the applicator in the mouth of the container, and a normally closed pressure-responsive valve for permitting the flow of fluid (the composition) from the container to the applicator upon the application of pressure to the valve. The valve can include a diaphragm formed from an elastically fluid impermeable material with a plurality of non-intersecting arcuate slits therein, where each slit has a base which is intersected by at least one other slit, and where each slit is out of intersecting relation with its own base, and wherein there is a means for disposing the valve in the container inside of the applicator. Examples of these applicator devices are described in U.S. Pat. No. 4,693,623, to Schwartzman, issued Sep. 15, 1987; U.S. Pat. No. 4,620,648, to Schwartzman, issued Sep. 15, 1987; U.S. Pat. No. 2,669,323, to Harker et al., issued Jun. 13, 1972; U.S. Pat. No. 3,418,055, to Schwartzman, issued Dec. 24, 1968; and U.S. Pat. No. 3,410,645, to Schwartzman, issued Nov. 12, 1968; all of which are incorporated herein by reference in their entirety. Examples of applicators useful herein are commercially available from Dab-O-Matic, Mount Vernon, N.Y.

C. Cathodal iontophoresis

Where the primary active comprises a negatively-charged active, e.g. the cyclic polyanionic polyols, another preferred method of the subject invention involves application of a safe and effective amount of the primary actives in a conductive cream or gel, followed by controlled application of an electric field having a polarity such as to drive the negatively-charged active into the skin. This method, known as cathodial iontophoresis, is described in A. K. Banga and Y. W. Chien, "Iontophoretic Delivery of Drugs; Fundamentals, Developments, and Biomedical Applications" *J. Controlled Release* Vol. 7, pp. 1–24 (1988) and reference therein, incorporated herein by reference. Further examples are given in R. R. Burnett, "Iontophoresis," J. Hadgraft and R. H. Guy (editors), *Transdermal Drug Delivery; Development Issues and Research Initiatives,* Marcel Dekker, New York, N.Y. 1989, pp. 247–291 and references therein and in G. B. Kasting, E. W. Merritt, and J. C. Keister, "An In Vitro Method for Studying the Iontophoretic Enhancement of Drug Transport Through Skin," *Journal of Membrane Science,* Vol. 35, pp. 137–159, (1988), and reference therein, incorporated herein by reference. In such a method the composition is applied to the skin and contacted by the cathode of an electrical device suitable for delivering a controlled voltage or current to the skin. The circuit is completed by placing the anode of the device on the skin at a point removed from the site of delivery. The electrical field (i.e., voltage or current) may be either pulsed, sinusoidal, or continuous wave as described in the above references. The duration of application of the field ranges from about 1 minute to about 24 hours, preferably from about 1 to about 30 minutes, more preferably from about 2 to about 5 minutes. A series of high voltage pulses followed by continuous cathodic iontophoresis as described in M. R. Prausnitz, V. G. Bose, R. Langer, and J. C. Weaver, "Electroporation of Mammalian Skin: A Mechanism to Enhance Transdermal Drug Delivery," *Proceedings of the National Academy of Sciences* (*USA*), Vol. 90, pp. 10504–10508, (1993) and references therein, incorporated herein by reference, may also be used. In all cases the electric field is applied in a safe and effective manner, so that the anionic active is delivered across the skin without undue discomfort or irritation to the subject.

Methods For Improving the Visual Appearance of Skin

The subject invention relates to methods of improving the visual appearance of skin. Such methods comprise topically applying to the skin an effective amount of the compositions of the subject invention so as to deposit an effective amount of the primary actives on the skin. The term "effective amount", as used herein, means an amount sufficient to provide a skin appearance benefit as defined herein after single or multiple application, generally multiple application. In general, a safe and effective amount of the primary actives are left in contact with the skin for a period sufficient to provide noticeable benefits after single or multiple application, typically multiple application such as described herein. Typically, the primary actives are left in contact with the skin for a period of at least several hours (e.g. about 4 to about 12 hours) before washing of the skin might be done. The composition can be applied for several hours, days, weeks, months or years at appropriate intervals. The compositions are preferably applied from about three times a day to about once every three days, more preferably from about twice a day to once every other day, also preferably about once a day until a satisfactory skin appearance improvement has been achieved. Improvements in skin appearance may be observed with or without magnification by a variety of methods such as are known in the art, including image analysis, expert grading, self assessment, replicas, and histology. Exemplary methods of assessing improvements in skin appearance are described by Warren et al. in "Age, Sunlight, and Facial Skin: A Histologic and Quantitative Study", the Journal of the American Academy of Dermatology, 1991; 25: 751–60, which is incorporated herein by reference.

Typically, in each application, an effective coating of the skin with the primary actives is achieved by topically applying (in terms of mg active/cm$^2$ skin) from about 0.001 mg/cm$^2$ of a sulfhydryl compound, and from about 0.004 mg/cm$^2$ to about 0.1 mg/cm$^2$ of zwitterionic surfactant having structure (I). More preferably, from about 0.02 mg/cm$^2$ to about 0.06 mg/cm$^2$ of each of the primary actives is applied. For example, about 0.04 mg/cm$^2$ of each of the primary actives may be applied.

The compositions can be used as a leave-on product or the skin may be rinsed soon after application of the compositions to the skin, e.g., compositions in the form of rinse-off cleansers.

The compositions are generally applied by lightly massaging the composition into the skin, which may or may not be followed by cathodal iontophoresis.

EXAMPLES

The following examples further describe and demonstrate embodiments within the scope of the subject invention. The examples are given solely for the purpose of illustration and are not to be construed as limitations of the subject invention, as many variations thereof are possible without departing from the spirit and scope of the invention.

EXAMPLE 1

A skin cream is prepared from the following components

| INGREDIENT | PHASE CODE | WEIGHT % in PRODUCT |
| --- | --- | --- |
| Sterile Water | A | 54.48 |
| Disodium EDTA | A | 0.250 |
| Methyl Paraben | A | 0.150 |
| Glycerin | A | 3.00 |

-continued

| INGREDIENT | PHASE CODE | WEIGHT % in PRODUCT |
|---|---|---|
| Natrosol Plus CS 330 (modified hydroxyl ethyl cellulose from Aqualon) | A | 0.200 |
| Polypropylene glycol-15 stearyl ether | B | 3.250 |
| Propyl Paraben | B | 0.100 |
| Cetyl Alcohol | B | 0.559 |
| Stearyl Alcohol | B | 2.027 |
| Behenyl Alcohol | B | 0.221 |
| Steareth-21 | B | 0.366 |
| Steareth-2 | B | 1.097 |
| Distearyldimonium chloride | B | 0.950 |
| N-acetyl-L-Cysteine | C | 2.00 |
| Zinc Oxide | C | 0.10 |
| Phytic Acid, dipotassium salt | C | 5.00 |
| Cetyl Betaine | C | 1.50 |
| Methyl Paraben | C | 0.10 |
| Disodium EDTA | C | 0.05 |
| 50% NaOH | C | 3.50 |
| 1 M NaOH | C | Adjust pH |
| Sterile Water | C | 17.75 |
| DC Q2-1401 (cyclomethicone/dimethiconol-50/50 blend) | D | 0.750 |
| polyethylene Low Density Beads in DC200/10 Fluid (1:1 mix) | D | 2.00 |
| Benzyl Alcohol | D | 0.50 |
| Fragrance | D | 0.10 |

Blend the A, B, C, and D phase components separately with a mixer. Heat the A phase and B phase mixtures separately with stirring to 65°–75° C., then combine and blend and homogenize these phases with a mixer followed by a colloid mill. Cool the A phase plus B phase mixture to 45°–50° C. Bring the C phase mixture to pH 5. Add the C phase and D phase mixtures to the A phase plus B phase mixture and blend with a mixer. Adjust the final pH to 5.5.

The product is applied to the face and neck at a level of 1 mg/cm$^2$ twice daily for 6 months, resulting in reduced appearance of fine lines and wrinkles and a reduction in age spots.

EXAMPLES 2–7

Prepare a simple solution by combining the following components using conventional mixing techniques:

| COMPONENT | 2 | 3 | 4 | 5 | 6 | 7 |
|---|---|---|---|---|---|---|
| myo-inositol hexakis phosphoric acid (phytic acid), 50% solution in water | 1 | — | — | 5 | 5 | 5 |
| myo-inositol hexakissulfate, hexapotassium salt | — | 2 | — | — | — | — |
| sucrose octasulfate, octasodium salt | — | — | 5 | — | — | — |
| N-acetyl-L-cysteine | 0.5 | 0.5 | 0.5 | 2 | — | — |
| dithiothreitol | — | — | — | — | 1 | — |
| glutathione | — | — | — | — | — | 0.5 |
| cetyl betaine | 0.5 | 1 | 1 | — | — | — |
| cocoamidopropyl betaine | — | — | — | 1 | 1 | 1 |
| 99% triethanolamine | 2 | — | — | 10 | 10 | 10 |
| phosphoric acid, 85% | — | 0.25 | 1.0 | — | — | — |
| propylene glcyol | 20 | 20 | 20 | 20 | 20 | 20 |
| ethanol, absolute | 10 | 10 | 10 | 10 | 10 | 10 |
| deionized water | Balance to 100% | | | | | |

Apply the composition to the skin at a level of 1 mg/cm$^2$ once per day for a period of three months to regulate skin wrinkles. Use cathodic iontophoresis for 2 minutes per application at a current density of 0.050 ma/cm$^2$ to enhance regulation of skin wrinkles.

EXAMPLES 8–11

Prepare an oil-in-water emulsion by combining the following components using conventional mixing techniques.

| COMPONENT | 8 | 9 | 10 | 11 |
|---|---|---|---|---|
| Arg—Lys—Arg | 0.1 | — | — | — |
| Ac—Arg—Lys—Arg—NH$_2$ | — | 0.1 | — | — |
| His—Gly—Gly | — | — | 0.5 | — |
| His—Gly—Gly Cu complex (lamin) | — | — | — | 0.5 |
| N-acetyl-L-cysteine | 2 | 2 | 2 | 2 |
| Stearyl betaine | 1 | 1 | 1 | 1 |
| Glycerin | 3 | 3 | 3 | 3 |
| Methyl paraben | 0.2 | 0.2 | 0.2 | 0.2 |
| Steareth 20 (Brij 78R) | 1 | 1 | 1 | 1 |
| Glycerol monostearate and PEG 100 (Arlacel 165R) | 0.5 | 0.5 | 0.5 | 0.4 |
| Carbopol 940 | 0.2 | 0.2 | 0.2 | 0.2 |
| Cetyl alcohol | 1 | 1 | 1 | 1 |
| Stearyl alcohol | 1 | 1 | 1 | 1 |
| Propyl paraben | 0.1 | 0.1 | 0.1 | 0.1 |
| Di-isopropyl dimerate | 2 | 2 | 2 | 2 |
| C$_{12}$-C$_{15}$ alcohol benzoate | 6 | 6 | 6 | 6 |
| Imidazolidinal urea | 0.3 | 0.3 | 0.3 | 0.3 |
| Ammonium hydroxide, 30% solution | 1.6 | 1.6 | 1.6 | 1.6 |
| Deionized Water | Balance to 100% | | | |

Apply the composition to the skin at a level of 2 mg/cm$^2$, three times per day for one year to regulate skin wrinkles

EXAMPLES 12–15

Prepare a clear gel by combining the following components utilizing conventional mixing techniques

| COMPONENT | 12 | 13 | 14 | 15 |
|---|---|---|---|---|
| Lysophosphatidic acid | 0.5 | — | — | — |
| Fluorolysophosphatidic acid | — | 0.5 | — | — |
| Beta-cyclodextrin tetradecasulfate | — | — | 2 | — |
| Sulfobutyl beta-cyclodextrin | — | — | — | 2 |
| Dithioerythritol | 0.2 | 0.2 | 0.2 | 0.2 |
| Cetyl propyl hydroxy sultaine | 0.5 | 0.5 | 0.5 | 0.5 |
| Carbopol 980 | 0.55 | 0.5 | 0.5 | 0.5 |
| Disodium EDTA | 0.02 | 0.02 | 0.02 | 0.02 |
| 99% triethanolamine | 2 | 1.2 | 2 | 1.2 |
| Propylene glycol | 3 | 3 | 3 | 3 |
| Methyl paraben | 0.2 | 0.2 | 0.2 | 0.2 |
| Deionized Water | Balance to 100% | | | |

Apply the composition to the face and neck at a level of 1 mg/cm$^2$ twice per day for the subject's lifetime to regulate skin wrinkles.

EXAMPLES 16–21

Prepare an oil-in-water polymer emulsion by combining the following components using conventional mixing techniques.

| COMPONENT | 16 | 17 | 18 | 19 | 20 | 21 |
|---|---|---|---|---|---|---|
| myo-inositol hexakis phosphoric acid (phytic acid), dipotassium salt | 3 | — | — | — | — | — |
| Sorbitol sulfate | — | 3 | — | — | — | — |
| Trehalose sulfate | — | — | 3 | — | — | — |

-continued

| COMPONENT | EXAMPLE NO. | | | | | |
|---|---|---|---|---|---|---|
| | 16 | 17 | 18 | 19 | 20 | 21 |
| Heparin sulfate, MW approx. 7500 | — | — | — | 0.2 | — | — |
| Heparin, bovine, low molecular weight (ca. 3000) | — | — | — | — | 0.1 | — |
| Dermatan sulfate | — | — | — | — | — | 0.2 |
| N-acetyl-L-cysteine | 1 | 1 | 1 | 1 | 1 | 1 |
| Cetyl betaine | 1 | 1 | 1 | 1 | 1 | 1 |
| Carbopol 954 | 0.2 | 0.2 | 0.2 | 0.2 | 0.2 | 0.2 |
| Pemulen TR-2 | 0.15 | 0.15 | 0.15 | 0.15 | 0.15 | 0.15 |
| Glycerin | 3 | 3 | 3 | 3 | 3 | 3 |
| Cetyl palmitate | 2 | 2 | 2 | 2 | 2 | 2 |
| Stearoxy trimethylsilane and stearyl alcohol | 1 | 1 | 1 | 1 | 1 | 1 |
| Squalane | 6 | 6 | 6 | 6 | 6 | 6 |
| Propyl paraben | 0.1 | 0.1 | 0.1 | 0.1 | 0.1 | 0.1 |
| Methyl paraben | 0.2 | 0.2 | 0.2 | 0.2 | 0.2 | 0.2 |
| Imidazolidinol urea | 0.3 | 0.3 | 0.3 | 0.3 | 0.3 | 0.3 |
| Ammonium hydroxide, 30% solution | 5 | 3 | 5 | 3 | — | — |
| 99% triethanolamine | — | — | — | — | 0.35 | 0.35 |
| Deionized Water | Balance to 100% | | | | | |

Apply the composition to the skin once per week at a level of 5 mg/cm$^2$ over a three-year period to regulate skin wrinkles.

EXAMPLES 22–25

Prepare a finely divided oil-in-water emulsion by combining the following components using conventional mixing techniques.

| COMPONENT | EXAMPLE NO. | | | |
|---|---|---|---|---|
| | 22 | 23 | 24 | 25 |
| myo-inositol hexakisphosphate, dodecasodium salt | 1.5 | — | — | — |
| sucrose octasulfate, octasodium salt | — | 1.5 | — | — |
| Ac—Arg—Lys—Arg—NH$_2$ | — | — | 0.1 | — |
| Arg—Ser—Arg—Lys | — | — | — | 0.1 |
| cysteine | 0.5 | 0.5 | 0.5 | 0.5 |
| C$_{22}$ ammoniohexanoate | 1 | 1 | 1 | 1 |
| phosphoric acid, 85% solution | 0.4 | 0.2 | — | — |
| PEG4 sorbitan monolaurate | 22.5 | 22.5 | 22.5 | 22.5 |
| PEG5 sorbitan monooleate | 2.5 | 2.5 | 2.5 | 2.5 |
| Cetearyl octanoate | 25 | 25 | 25 | 25 |
| DMDM hydantoin and 3-iodo-2-propynylbutyl carbamate (Glydant Plus) | 0.2 | 0.2 | 0.2 | 0.2 |
| Deionized Water | Balance to 100% | | | |

Apply the composition to the skin at a level of 2 mg/cm$^2$ three time per week over a five-year period to regulate skin wrinkles.

While particular embodiments of the subject invention have been described, it will be obvious to those skilled in the art that various changes and modifications to the subject invention can be made without departing from the spirit and scope of the invention. It is intended to cover, in the appended claims, all such modifications that are within the scope of the subject invention.

What is claimed is:

1. A topical composition for improving the visual appearance of mammalian skin, comprising:
   a) actives comprising:
      (i) a safe and effective amount of a cyclic polyanionic polyol having the structure:

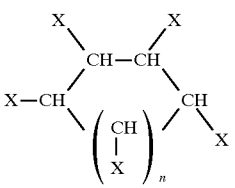

wherein:
   n is an integer from 1 to 3; and
   each X is, independently, selected from the group consisting of $OSO_3^-$, $SO_3^-$, $OPO_3^{2-}$, $PO_3^{2-}$, $CO_2^-$, and OH; and at least 3 X's are other than OH; and said composition comprises cations which balance the charge of said cyclic polyanionic polyol thereof;
   (ii) a safe and effective amount of a zwitterionic surfactant having the structure:

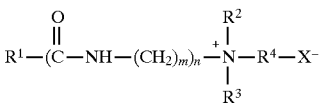

wherein:
   $R^1$ is unsubstituted, saturated or unsaturated, straight or branched chain alkyl having from about 9 to about 22 carbon atoms;
   m is an integer from 1 to 3;
   n is 0 or 1;
   $R^2$ and $R^3$ are, independently, alkyl having from 1 to about 3 carbon atoms, unsubstituted or mono-substituted with hydroxy;
   $R^4$ is saturated or unsaturated, straight or branched chain alkyl, unsubstituted or mono-substituted with hydroxy, having from 1 to about 5 carbon atoms; and
   X is selected from the group consisting of $CO_2$, $SO_3$ and $SO_4$; cosmetically acceptable salts of the foregoing compounds, and combinations thereof; and
   (iii) a safe and effective amount of a sulfhydryl compound selected from the group consisting of N-acetylcysteine, cysteine, glutathione, thioglycolic acid, thioglycolic acid ethyl ester, thiosalicylic acid, cysteamine, dithiothreitol, lipoic acid, dithioerythritol, thioacetic acid, thiolactic acid, mercaptoethanol, dimercaptol, monothioglycerol, N-(2-mercaptoproprionyl)glycine, bucillamine, mercaptometnthone, and combinations thereof; and
   b) a cosmetically acceptable topical carrier for said actives.

2. The composition of claim 1 wherein in said cyclic polyanionic polyo:
   a) n is 1 or 2; and
   b) each X is independently $OPO_3^{2-}$ or $OSO_3^-$.

3. The composition of claim 2 wherein each X is $OPO_3^{2-}$.

4. The composition of claim 3 wherein n is 2.

5. The composition of claim 1 wherein the composition comprises a cation selected from the group consisting of $H^+$, $Na^+$, $K^+$, $Ca^{++}$, $Mg^{++}$, $Al_2(OH)_5^+$, $NH_4^+$, $(HOCH_2CH_2)_3NH^+$, $(CH_3CH_2)_3NH^+$, $HOCH_2(CH_3)_2CNH_3^+$, $(HOCH_2)_3CNH_3^+$, $CH_3(HOCH_2)_2CNH_3^+$, $CH_3CH_2(HOCH_2)_2CNH_3^+$, $(CH_3CH_2)_4N^+$, $C_{16}H_{33}(CH_3)_3N^+$, $(N-C_{16}H_{33})C_5H_4N^+$, and combinations thereof.

6. The composition of claim 5 wherein the composition comprises a cation selected from the group consisting of $H^+$, $Na^+$, $NH_4^+$, $K^+$ or mixtures thereof.

7. The composition of claim 1 wherein said sulfhydryl compound is selected from the group consisting of N-acetyl-cysteine, glutathione, cysteine, thiosalicylic acid, lipoic acid, and combinations thereof.

8. The composition of claim 7 wherein said sulfhydryl compound is N-acetyl-cysteine.

9. The composition of claim 8 wherein said sulfhydryl compound is N-acetyl-L-cysteine.

10. The composition of claim 1 wherein said zwitterionic surfactant,
$R^1$ is unsubstituted, saturated or unsaturated, straight or branched chain alkyl having from about 9 to about 18 carbon atoms;
m is an integer from 1 to 3;
n is 0 or 1;
$R^2$ and $R^3$ are $CH_3$;
X is independently $CO_2$ or $SO_3$; and
$R^4$ is saturated or unsaturated, straight or branched chain alkyl, unsubstituted or mono-substituted with hydroxy, having from 1 to about 3 carbon atoms.

11. The composition of claim 10 wherein for said zwitterionic surfactant,
each X is $CO_2$; and
$R^4$ is $CH_2$.

12. The composition of claim 11 wherein for said zwitterionic surfactant,
$R^1$ is unsubstituted, saturated or unsaturated, straight or branched chain alkyl having from about 16 to about 18 carbon atoms; and
n is 0.

13. The composition of claim 1 wherein the zwitterionic surfactant is selected from the group consisting of behenyl betaine, cocoamidopropyl betaine, cetyl propyl hydroxy sultaine, cetyl betaine, stearyl betaine and combinations thereof.

14. The composition of claim 13 wherein said zwitterionic surfactant is selected from cetyl betaine, stearyl betaine, cocoamidopropyl betaine and combinations thereof.

15. The composition of claim 14 wherein said zwitterionic surfactant is cetyl betaine.

16. The composition of claim 14 wherein said zwitterionic surfactant is cocoamidopropyl betaine.

17. The composition of claim 1 wherein the composition comprises from about 0.01% to about 10% of said polar skin repair active, from about 0.1% to about 5% of said sulfhydryl compound, and from about 0.1% to about 5% of said zwitterionic surfactant.

18. A method of improving the smoothness of skin comprising topically applying to a mammal in need of such treatment the composition according to claim 1.

19. The method of claim 18 wherein:
(a) the amount of said polar skin repair active applied is from about 0.001 mg/cm² skin to about 0.5 mg/cm² skin;
(b) the amount of said sulfhydryl compound applied is from about 0.004 mg/cm² skin to about 0.1 mg/cm² skin; and
(c) the amount of said zwitterionic surfactant applied is from about 0.004 mg/cm² skin to about 0.1 mg/cm² skin.

20. A method of removing vellus hair from mammalian skin comprising topically applying to a mammal in need of such treatment the composition according to claim 1.

21. The method of claim 20 wherein:
(a) the amount of said polar skin repair active applied is from about 0.001 mg/cm² skin to about 0.5 mg/cm² skin;

(b) the amount of said sulfhydryl compound applied is from about 0.004 mg/cm² skin to about 0.1 mg/cm² skin; and
(c) the amount of said zwitterionic surfactant applied is from about 0.004 mg/cm² skin to about 0.1 mg/cm² skin.

22. A topical composition for improving the visual appearance of mammalian skin, comprising:
a) actives comprising:
(i) a safe and effective amount of a cyclic polyanionic polyo having the structure:

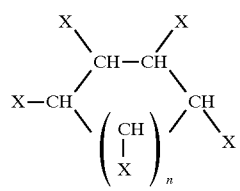

wherein:
n is an integer from 1 to 3; and
each X is, independently, selected from the group consisting of $OSO_3^-$, $SO_3^-$, $OPO_3^{2-}$, $PO_3^{2-}$, $CO_2^-$, and OH; and at least 3 X's are other than OH; and said composition comprises cations which balance the charge of said cyclic polyanionic polyo;
(ii) a safe and effective amount of a zwitterionic surfactant having the structure:

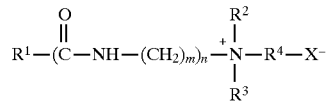

wherein:
$R^1$ is unsubstituted, saturated or unsaturated, straight or branched chain alkyl having from about 9 to about 18 carbon atoms;
m is an integer from 1 to 3;
n is 0 or 1;
$R^2$ and $R^3$ are $CH_3$;
X is independently $CO_2$ or $SO_3$; and
$R^4$ is saturated or unsaturated, straight or branched chain alkyl, unsubstituted or mono-substituted with hydroxy, having from 1 to about 3 carbon atoms; and
(iii) a safe and effective amount of a sulfhydryl compound selected from the group consisting of N-acetylcysteine, cysteine, glutathione, thioglycolic acid, thioglycolic acid ethyl ester, thiosalicylic acid, cysteamine, dithiothreitol, lipoic acid, dithioerythritol, thioacetic acid, thiolactic acid, mercaptoethanol, dimercaptol, monothioglycerol, N-(2-mercaptoproprionyl)glycine, bucillamine, mercaptomenthone, and combinations thereof; and
b) a cosmetically acceptable topical carrier for said actives.

23. The composition of claim 22 wherein for said cyclic polyanionic polyo:
n is 1 or 2; and
each X is independently $OPO_3^{2-}$ or $OSO_3^-$;
wherein said zwitterionic surfactant:
each X is $CO_2$;
$R^4$ is $CH_2$;

R$^1$ is unsubstituted, saturated or unsaturated, straight or branched chain alkyl having from about 16 to about 18 carbon atoms; and n is 0; and wherein said sulfhydryl compound is selected from the group consisting of N-acetyl-cysteine, glutathione, cysteine, thiosalicylic acid, lipoic acid, and combinations thereof.

24. The composition of claim 23 wherein for said cyclic polyanionic polyo:

each X is $OPO_3^{2-}$ and n is 2; said zwitterionic surfactant is selected from the group consisting of cetyl betaine and cocoamidopropyl betaine; and said sulfhydryl compound is N-acetyl-cysteine.

* * * * *

UNITED STATES PATENT AND TRADEMARK OFFICE
CERTIFICATE OF CORRECTION

PATENT NO.  : 5,821,237

DATED       : October 13, 1998

INVENTOR(S) : D. L. Bissett et al.

Page 1 of 5

It is certified that error appears in the above-identified patent and that said Letters Patent is hereby corrected as shown below:

Col. 1, line 29, "preventative," should read --preventative;--.

Col. 1, line 52, "is further" should read --is a further--.

Col. 1, line 59, "an/or" should read --and/or--.

Col. 2, line 22, "thiosalicyclic acid" should read --thiosalicylic acid--.

Col. 2, line 39, "carton" should read --carbon--.

Col. 3, line 65, "tin" should read --in--.

Col. 4, line 12, "here" should read --herein--.

Col. 4, line 49, "glycosaminoglylcans" should read --glycosaminoglycans--.

Col. 4, line 53, "cyclodextrins" should read --cyclodextrins,--.

Col. 4, line 66, " cyclodextris " should read --cyclodextrins,--.

Col. 5, line 19, "ore" should read --more--.

Col. 5, line 32, "$(CH_3CH_2)NH^+$" should read --$(CH_3CH_2)_3NH^+$--.

Col. 5, line 37, "ostasulfate," should read --octasulfate--.

Col. 6, line 22-23, "$(HOCH_2)CNH_3$" should read --$(HOCH_2)_3CNH_3$--.

Col. 7, line 24, "cetryltrimethylammonium" should read --cetyltrimethylammonium--.

Col. 8, line 49, "more" should read --most--.

Col. 8, line 53, "composition" should read --compositions--.

Col. 9, line 14, after "strontium salts;" please insert --non-toxic heavy metal salts, e.g., aluminum, and zinc salts; boron salts; silicon salts; --.

UNITED STATES PATENT AND TRADEMARK OFFICE
CERTIFICATE OF CORRECTION

PATENT NO. : 5,821,237
DATED : October 13, 1998
INVENTOR(S) : D. L. Bissett et al.

It is certified that error appears in the above-identified patent and that said Letters Patent is hereby corrected as shown below:

Col. 9, line 38, "olelyl" should read --oleyl--.

Col. 9, line 41, "ispropanol" should read --isopropanol--.

Col. 9, line 46, "glutahlione" should read --glutathione--.

Col. 9, line 50, "monothloglycerol," should read --monothioglycerol--.

Col. 10, line 52, "sulfhydryl" should read --sulfyhydryl--.

Col. 13, line 9, "et al.," should read --et al.;--.

Col. 13, line 15, "he" should read --the--.

Col. 13, line 37, "Segarin," should read --Sagarin,--.

Col. 13, line 45, "80% water," should read --80%, water;--.

Col. 13, line 49, "75% water," should read --75%, water;--.

Col. 13, line 54, "(oleginous)" should read --(oleaginous)--.

Col. 13, line 56, "emulsion," should read --emulsions;--.

Col. 13, line 58, "*Cosmetics*" should read --*Cosmetics,*--.

Col. 13, line 60, "here" should read --herein--.

Col. 14, line 39, "have" should read --having--.

Col. 15, line 43, "Most" should read --More--.

Col. 16, line 20, "here" should read --herein--.

Col. 16, line 30, "glcol" should read --glycol--.

Col. 16, line 51, "5,296,600," should read --5,296,500,--.

Col. 17, line 34, "fludocortisone," should read --fludrocortisone,--.

Col. 17, line 34, "privalate," should read --pivalate,--.

Col. 17, line 36, "fluocotolone," should read --fluocortolone,--.

Col. 17, line 38, "tramcinolone" should read --triamcinolone--.

UNITED STATES PATENT AND TRADEMARK OFFICE
CERTIFICATE OF CORRECTION

PATENT NO. : 5,821,237
DATED : October 13, 1998
INVENTOR(S) : D. L. Bissett et al.

It is certified that error appears in the above-identified patent and that said Letters Patent is hereby corrected as shown below:

Col. 17, line 39, "fluctonide," should read --flucetonide,--.

Col. 17, line 41, "difluorosone" should read --difluorosone--.

Col. 17, line 44, "clorotelone," should read --clocortelone,--.

Col. 17, line 45, "difluprednate," should read --diflurprednate,--.

Col. 17, line 45, "floromethalone," should read --fluoromethalone,--.

Col. 17, line 49, "beciomethasone" should read --beclomethasone--.

Col. 17, line 49, "trimcinolone," should read --triamcinolone,--.

Col. 18, line 4, "tometin," should read --tolmetin,--.

Col. 18, line 7, "mefanamic," should read --mefenamic,--.

Col. 18, line 11, "piroprofen," should read --pirprofen,--.

Col. 18, line 12, "microprofen," should read --miroprofen,--.

Col. 18, line 29, "pants" should read --plants--.

Col. 19, line 10, "peeling" should read --peeling,--.

Col. 19, line 10, "agent" should read --age--.

Col. 19, line 27, "(umbeliferone," should read --(umbelliferone,--.

Col. 19, line 32, "2-naphtol-3,6-disulfonic" should read --2-naphthol-3,6-disulfonic--.

Col. 19, line 38, "olcate," should read --oleate--.

Col. 19, line 53, "digalloyltrioleaic," should read --digalloyltrioleate,--.

Col. 19, lines 56-57, "3,3,5-tir-methylcyclo-hexylsalicylate," should read --3,3,5-tri-methylcyclohexylsalicylate--.

Col. 19, line 63, "Most" should read --More--.

UNITED STATES PATENT AND TRADEMARK OFFICE
CERTIFICATE OF CORRECTION

PATENT NO.  : 5,821,237
DATED       : October 13, 1998
INVENTOR(S) : D. L. Bissett et al.

It is certified that error appears in the above-identified patent and that said Letters Patent is hereby corrected as shown below:

Col. 19, line 65, "butylmethoxydibenzoylmethan," should read --butylmethoxydibenzoylmethane--.

Col. 20, line 18, after "ester of 2-hydroxy-4-(" please insert --(2-hydroxyethoxy)benzophenone; 4-N,N-(2-ethylhexyl)-methylaminobenzoic acid ester of 4-(--.

Col. 20, line 26, "sue of" should read --use of a--.

Col. 20, line 46, "glutahione" should read --glutathione--.

Col. 20, line 53, "radiation" should read --UV radiation--.

Col. 21, line 2, "it" should read --its--.

Col. 21, line 13, "and" should read --other--.

Col. 21, line 37, "Bjush" should read --Bush--.

Col. 21, line 44, "furldioxime," should read --furildioxime--.

Col. 21, line 50, "deferoxamine," should read --deferoxamine;--.

Col. 22, line 15, "as" should read --at--.

Col. 22, line 20-21, "examplary" should read --exemplary--.

Col. 22, line 47, "method" should read --methods--.

Col. 22, line 64, "an" should read --and--.

Col. 23, line 16-17, "2,669,323" should read --3,669,323--.

Col. 23, line 30, "cathodial" should read --cathodal--.

Col. 23, line 31, "Drugs;" should read --Drugs:--.

Col. 23, line 34, "reference" should read --references--.

Col. 23, line 37, "*Delivery; Development*" should read --*Delivery: Developmental*--.

Col. 23, line 43, "reference" should read --references--.

UNITED STATES PATENT AND TRADEMARK OFFICE
CERTIFICATE OF CORRECTION

PATENT NO. : 5,821,237
DATED : October 13, 1998
INVENTOR(S) : D. L. Bissett et al.

It is certified that error appears in the above-identified patent and that said Letters Patent is hereby corrected as shown below:

Col. 24, line 12, "e.g." should read --e.g.,--.

Col. 24, line 26, "Study"," should read --"Study";--.

Col. 24, line 33, after "mg/cm$^2$" please insert --to about 0.25 mg/cm$^2$ of polar skin repair active, from about 0.004mg/cm$^2$ to about 0.1 mg/cm$^2$ --.

Col. 24, line 41, "compositions" should read --composition--.

Col. 28, line 49, "mercaptometnthone," should read --mercaptomenthone--.

Col. 28, line 53, "polyo" should read --polyol--.

Col. 30, line 11, "polyo" should read --polyol--.
Col. 30, line 28, "polyo" should read --polyol--.

Col. 30, line 61, "polyo" should read --polyol--.

Col. 32, line 2, "polyo" should read --polyol--.

Signed and Sealed this

Seventeenth Day of October, 2000

*Attest:*

Q. TODD DICKINSON

*Attesting Officer*     *Director of Patents and Trademarks*